United States Patent [19]

Hall

[11] Patent Number: 4,900,150

[45] Date of Patent: Feb. 13, 1990

[54] MULTIPLE INPUT SOURCE TECHNIQUE FOR DERIVING CAVITY LINEWIDTH

[75] Inventor: David B. Hall, LaCrescenta, Calif.

[73] Assignee: Litton Systems, Inc., Beverly Hills, Calif.

[21] Appl. No.: 199,858

[22] Filed: May 27, 1988

[51] Int. Cl.[4] ............................................... G01B 9/02
[52] U.S. Cl. ..................................... 356/349; 356/352
[58] Field of Search ................ 356/345, 346, 349, 352

[56] References Cited

PUBLICATIONS

V. E. Sanders, "High-Precision Reflective Measurement Technique for Low-Loss Laser Mirrors," Applied Optics, vol. 16, p. 19, Jan. 1977.
D. Z. Anderson et al., "Mirror Reflectometer Based on Optical Cavity Decay Time," Applied Optics, vol. 23, p. 1238, Apr. 1984.
D. A. Smith et al., "Simple Measurement of Gain and Loss in Ultralow Optical Resonators," Applied Optics, vol. 24, p. 1722, Jun. 1985.

Primary Examiner—Davis L. Willis
Assistant Examiner—Matthew W. Koren
Attorney, Agent, or Firm—Poms, Smith, Lande & Rose

[57] ABSTRACT

A variety of techniques for deriving cavity linewidth that share the use of multiple input sources of known frequency separation is disclosed allowing the measurement of resonator cavity linewidth. Among the techniques include a double peak ratio method for measuring cavity linewidth through use of a low pass filter. The double peak ratio method allows vertical measurements which are noise immune and independent of swept frequency errors as a method of determining cavity linewidth in a straightforward and accurate manner.

9 Claims, 3 Drawing Sheets

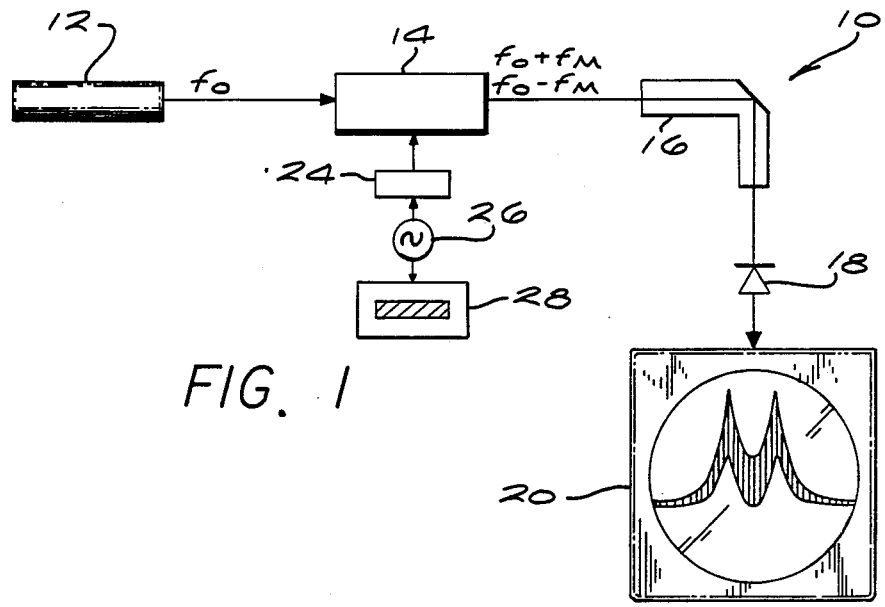
FIG. 1
FIG. 2
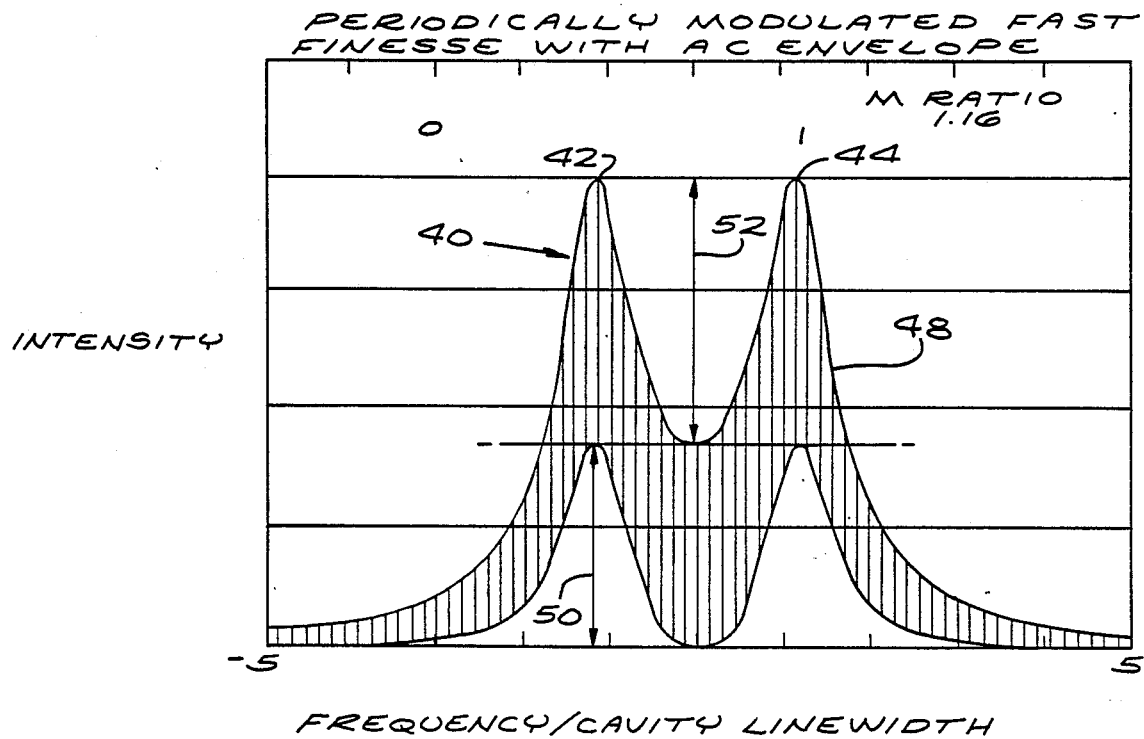

MULTIPLE INPUT SOURCE TECHNIQUE FOR DERIVING CAVITY LINEWIDTH

BACKGROUND OF THE INVENTION

(1) Field of the Invention

This invention relates to measurement techniques for determining cavity linewidth of a passive resonator cavity. More particularly, this invention relates to a method for measuring cavity linewidth of a passive resonator which uses a multiple input radiation source to perform such measuring techniques.

(2) Description of Related Art

Heretofore, passive resonator cavities, either linear or ring-configured, have had their cavity linewidth measured according to conventional techniques such as fast finesse and ringdown.

In the fast finesse technique, a series of resonant peaks are displayed on an oscilloscope. The signal shown is detected from the output of a resonator where a coherent radiation source, such as a laser, has injected radiation into the resonator cavity being measured. The output display for fast finesse technique (in the prior art) displayed a series of peaks separated by a distance known as the free spectral range (FSR), as a result of sweeping a piezoelectric transducer (PZT) initially through at least a GHz at a rate of about 30 Hz. This sweeping may be done at the source or the resonant cavity. The free spectral range is the separation in frequency (hertz) between two adjacent longitudinal modes such as Q and Q+1. The free spectral range is usually equal to C divided by L, where C is the speed of light and L is the ring resonator cavity length. Where a linear cavity is being measured, free spectral range is related to C/2L. Using the fast finesse technique, this free spectral range must be measured empirically by reference to the oscilloscope display of the experimental configuration. Additionally, fast finesse technique required a measurement of linewidth measured as FWHM or Full Width at Half-Maximum power. When both of these empirical measurements are made, the finesse of the resonator cavity may be determined by the ratio of free spectral range divided by linewidth. Thus, fast finesse technique required two separate empirical measurements. Both free spectral range and linewidth had to be separately measured in order to provide proper information as to the resonant frequency of the passive cavity. An error in either measurement could introduce error in the derived finesse.

Likewise, the ringdown technique involves the examination of a resonant cavity wherein short pulses are injected into the cavity. The decay time of the short pulses trapped within the cavity is a measure of cavity loss. The output signal on the oscilloscope may be used to make the necessary measurements.

SUMMARY OF THE INVENTION

A method of measuring cavity linewidth of a passive resonator, such as a linear and ring cavity, is disclosed. This method comprises the steps of introducing a coherent split frequency radiation signal into a passive resonator. The split frequency radiation signal is itself divided into a plurality of modes adjacent to one another and separated by a known uniform frequency spread which may be a function of cavity length in that the spread is sufficiently separated between modes so that adjacent modes have minimal overlap. This split frequency source of radiation for the cavity may be derived by modulating the output of a coherent radiation signal from a swept frequency laser. Alternatively, frequency splitting may be achieved by use of a Zeeman laser, where a uniform magnetic field is applied to the active region of the laser so that the output results in two or more modes of a predetermined frequency separation.

After this split-frequency radiation signal has been introduced into the passive resonator, the output from the cavity is detected as a cavity output radiation signal. This signal is then processed for analysis on a display terminal. In this manner passive resonator cavity linewidth may be determined.

A first method of cavity linewidth measurement uses a display terminal to show a double peak signal that is symmetric about a central vertical axis where the double peak signal is part of a modulation envelope. This signal is adjusted so that the known frequency difference between adjacent peaks (otherwise known as the modulation frequency) is typically less than one cavity linewidth separation. The separation distance between the peaks is twice the modulation frequency of the electro-optic modulator and may be read off the display, as well as cavity linewidth (full width at half-maximum). A measurement of free spectral range is no longer necessary to obtain the finesse. When the height of the peak under the envelope is aligned on the Y axis with the dip between the peaks on the top of the envelope, the cavity linewidth is equal to the modulation drive frequency divided by 1.16 for a detector with a flat frequency response. This height comparison is all that is needed to obtain cavity finesse, along with reading frequency off a frequency counter. This single vertical comparison replaces taking two horizontal measurements as required in the prior art.

A preferred embodiment of the invention is one in which the display terminal shows a vertically symmetrical double peak signal without a modulation envelope. A ratio is measured between the vertical height of the double peaks of the output signal profile and the central vertical height of the dip between the peaks, allowing the derivation of a dip-to-peak ratio. This dip-to-peak ratio is then applied to an algorithm or curve from which a cavity linewidth measurement may be determined. Thus, the preferred method of cavity linewidth measurement requires the measurement of vertical information on the oscilloscope screen, i.e., the ratio between peak and dip height relative to a preference baseline. This vertically directed information is less susceptible to noise interference than methods in the prior art.

A third embodiment of this invention is directed to a display terminal where a series of resonant peaks are separated by a known uniform frequency spread. The full width at half-maximum of one peak is measured as is the separation between it and an adjacent peak. In this manner, cavity linewidth may be easily derived with but two horizontal measurements.

BRIEF DESCRIPTION OF THE DRAWINGS

The particulars of the configuration of each of the experimental units which carry out the methods disclosed in this invention will be described more fully with reference to the accompanying drawings and detailed description of the preferred embodiment, wherein:

FIG. 1 is a schematic diagram of a circuit that produces a double peak oscilloscope display of a modulation envelope;

FIG. 2 is an enlarged view of the oscilloscope display showing the double peak modulation envelope;

DETAILED DESCRIPTION OF THE PREFERRED EMBODIMENT

Figure 3:
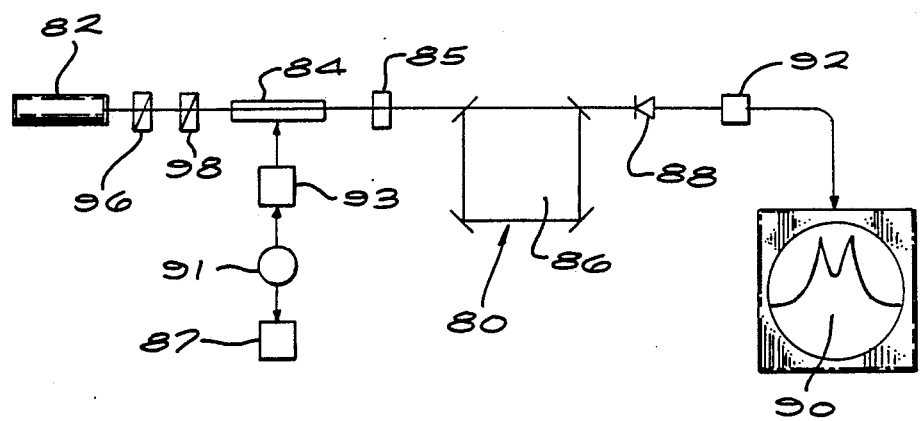
FIG. 3 is a schematic diagram similar to FIG. 1 illustrating a circuit that produces a double peak without a modulation envelope.

With reference to FIG. 1, a schematic is shown for producing the display shown in FIG. 2 having a double peaked, modulated envelope. A swept frequency laser 12 may be dithered at a rate of 20 to 30 hertz by use of a piezo-electric transducer (not shown), deriving a central carrier frequency ($f_0$) which is substantially coherent. The output signal of the source laser 12 in the preferred embodiment is an electromagnetic wave in the optical region. However, this invention need not be restricted to the optical region, but the configuration shown makes use of a laser in the optical range of the electromagnetic spectrum for purposes of illustration. This carrier frequency ($f_0$) is applied in this embodiment to an electro-optical modulator 14, such as a Pockel cell. The resultant frequency output includes a frequency upshifted and downshifted from the central frequency by a factor of ($fm$). These sideband frequencies are then introduced into a resonator cavity 16 whose cavity linewidth is to be measured. The output signal from the resonator cavity 16 is detected by a detector 18 and a display of that output signal is provided on an oscilloscope 20.

The electro-optic modulator 14 may be driven by an oscillator 26, whose signal is amplified by an amplifier 24 and applied to the modulator 14. The oscillator also has a frequency counter 28 to indicate the frequency at which the oscillator 26 is driven. It is understood that, while FIG. 1 shows a substantially linear resonator 16, a ring cavity may also be tested.

In FIG. 1, the carrier frequency ($f_0$) is eliminated by using a D.C. bias applied to the modulator 14. This creates a variable wave plate within the modulator which receives the linearly polarized light from the laser 12. The crystal of the modulator 14 is oriented at 45° to the linear polarized light. The cavity 16 is then oriented to eliminate the carrier but to retain the two side bands.

By proceeding according to the configuration shown in FIG. 1, a frequency shift is provided to the output signal which is equal to the modulator drive frequency. This method demonstrates a technique for measuring cavity linewidth by sending a frequency swept beam from a source laser through an electro-optic modulator which divides the light equally into one upshifted and one downshifted component and eliminates the carrier. The frequency shift ($fm$) is then equal to the modulator drive frequency. This twin frequency signal generates a two peak resonance when propagated through the passive cavity 16 under test. The two peak resonant display is shown at 40 of FIG. 2. This technique provides a new method to obtain cavity linewidth measurement, in that two transmission peaks are shown instead of the single peak used in the prior art.

When the modulation frequency is less than one cavity linewidth, the two peaks 42 and 44 (FIG. 2) in the display are distinct but not completely separated. With reference to FIG. 2, the shaded portion 48 of the display 40 forms a modulation envelope. When the height of the peak under the envelope 50 is substantially equal to and aligned on the Y axis with the dip between the two peaks on the top of the envelope 52, it has been empirically and mathematically determined that the cavity linewidth is equal to the modulation drive frequency divided by 1.16 ($fc=fm/1.16$) for a detector with a flat frequency response. This single height comparison and the reading of the modulation frequency ($fm$) from the counter 28 are all that is needed to obtain cavity linewidth.

Using the appropriate D.C. bias, the A.C. modulation of the modulator 14 suppresses the carrier ($f_0$) and produces a balanced pair of sidebands with peaks at 42 and 44, FIG. 2. Measurements have been made using the configuration shown in FIG. 1 on a 20 cm. length (L) cavity. The envelope heights are most closely matched for a 20 cm. cavity at 113 kHz. When the 113 kHz. signal is divided by a derived ration of 1.125 (derived from the 1.16 ratio previously mentioned), the resulting cavity linewidth is measured to be 100.4 kHz. Measuring this cavity by use of the ringdown method of the prior art produced a measurement of 100 kHz, while conventional fast finesse techniques measured a cavity linewidth of 107 kHz.

Figure 4A:
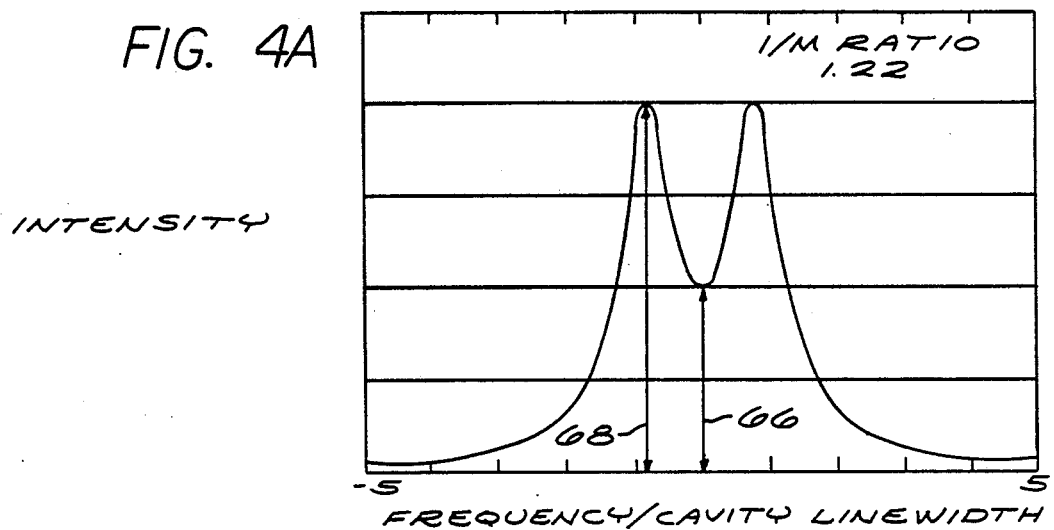
FIG. 4A shows an oscilloscope display for a double peak envelope having no modulation.
Figure 4B:
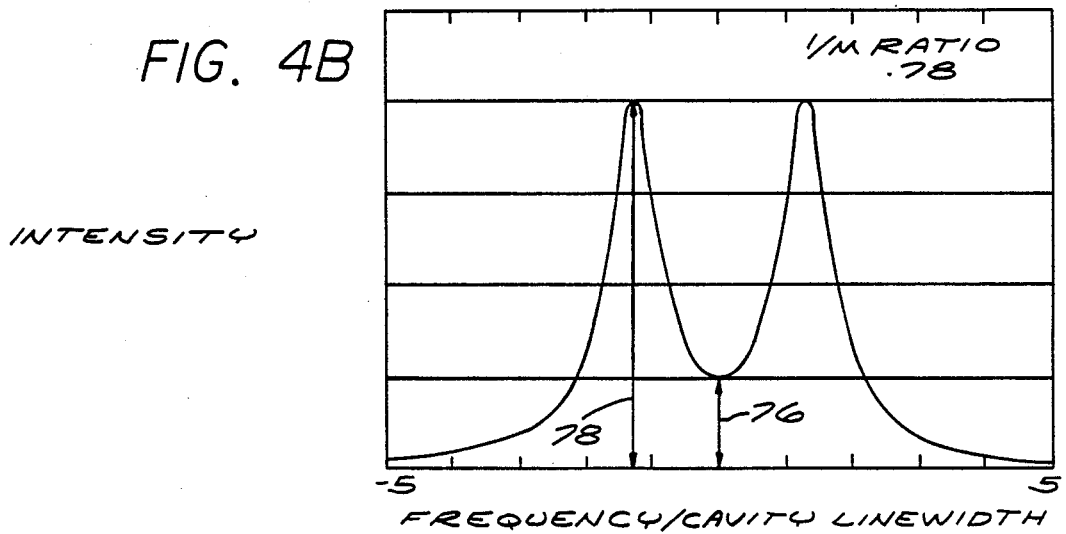
FIG. 4B shows another envelope similar to FIG. 4A.

FIGS. 3, 4A and 4B show a method and configuration for performing a cavity linewidth measurement which eliminates the A.C. modulation envelope used in FIG. 1 and replaces the D.C. bias with wave plates.

With particular reference to FIG. 3, a schematic is shown which will produce a double peak signal on the display of an oscilloscope 90 of the system shown at 80. In this preferred embodiment, a coherent laser source 82 provides an output carrier signal to a modulator 84 for injection into a resonator ring cavity 86. The signal from the laser 82 passes through a half wave plate 96 and a quarter wave plate 98, which are appropriately rotated in combination with modulator 84 to eliminate the carrier. Once light passes through the modulator 84, it enters a polarizer 85 before being introduced into a resonator ring cavity 86. Output from the ring cavity is passed a through an electronic detector 88 and a low pass filter 92 before being displayed on the oscilloscope 90. As before, the electro-optical modulator 84 is driven by a voltage oscillator 91 whose output signal is amplified by an amplifier 93. The oscillator is also used as a source of a frequency counter display shown at 87. By passing the detected signal from the detector 88 through the low pass filter 92, before display upon the oscilloscope 90, the A.C. modulation envelope seen in FIG. 2 can be eliminated from the display as shown at FIGS. 4A and 4B. This signal is subject to less movement or jitter and is thus easier to measure. The signal is also subject to less system noise. The resulting double peak signal is useful to determine a double peak ratio which is used for direct cavity linewidth measurement.

Figure 5:
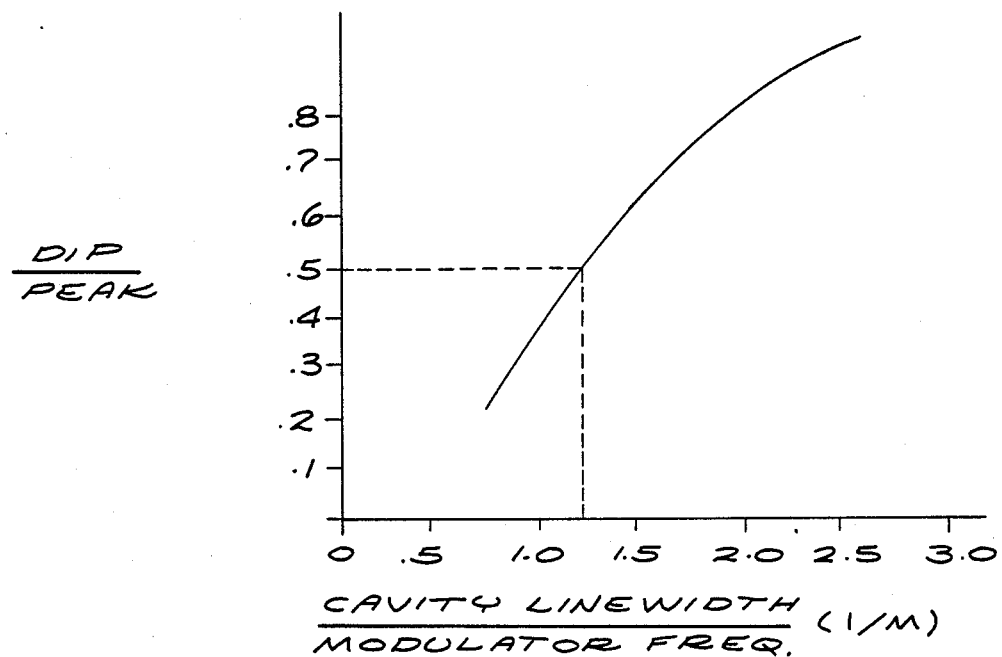
FIG. 5 is a curve used to determine cavity linewidth from the measurements made in FIGS. 4A and 4B.

By eliminating the A.C. envelope, cavity linewidth may be measured by making use of a ratio between the vertical height of the dip between peaks 66 (FIG. 4A) over the vertical peak height 68. A reading of the modulator drive frequency from the counter 87 is then multiplied by a derived ratio known as the 1/M ratio which results from comparing the dip over peak ratio on the curve of FIG. 5. In FIG. 4A, a ratio of the dip 66 over the peak height 68 produces a ratio of 0.5. This ratio, when applied to the curve of FIG. 5, yields a 1/M ration of 1.22. This 1/M ratio when multiplied by the modulator drive frequency reading from the counter 87 yields the cavity linewidth.

FIG. 4B shows another measurement where the central dip is deeper. FIG. 4B shows a wave form where height of the symmetrically displaced peaks is measured along the distance 78. The measurable dip height 76 yields a ration of 0.25 which, when applied to the curve of FIG. 5, converts to a 1/M ratio of 0.78. The double peak technique for cavity linewidth shown in FIGS. 3, 4A, 4B and 5 shows agreement between this technique and prior art techniques within an accuracy of ±10 percent. In fact, the accuracy would be closer is it were not for the variability of conventional fast finesse techniques for measuring cavity linewidth.

The double peak ratios are reliable and extremely reproducible. In fact, these results are more reproducible than the full width at half-maximum measurements derived by conventional fast finesse techniques. The double peak ratio measurements do not depend upon the linearity of the laser sweep. The relative vertical heights of voltage amplitude are more accurate, as opposed to the horizontal measurements of either time or sweep voltage. This is because the vertical heights are independent of the varying sweep laser speed for sufficiently low speeds. Thus, the inaccuracies which creep into measurement in a conventional horizontal full width at half-maximum measurement is avoided. In this manner, the 1/M ratio measurement is much more immune to noise than the full width at half-maximum (FWHM) associated with standard techniques. Attenuation of the beams by factors of more than 20 can degrade the double peak wave form substantially without affecting the ratio measurement. The dominant noise contribution from phase fluctuations does not affect the instantaneous signal amplitude to the first order. In making a double peak sweep, phase fluctuations will affect the horizontal location of peak and dip amplitudes, but not the sizes of these amplitudes.

Figure 6:
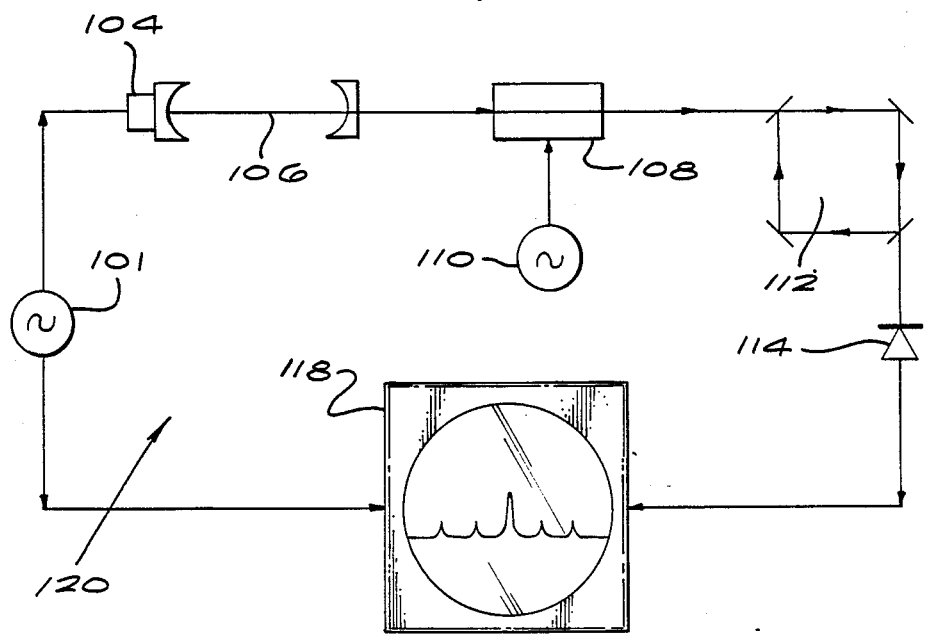
FIG. 6 shows a schematic diagram of an alternative method of the invention.

The system shown at 120 of FIG. 6 is directed to a schematic for deriving an output signal on the display scope 118 in which the distances between adjacent peaks are a predetermined amount, related to the frequency drive from the modulator 110. In this alternative embodiment, the laser source 106 is provided with a swept frequency drive 101 through a piezo-electric transducer 104 at one of the laser source mirrors. This swept frequency beam is then applied to a periodic modulator 108 such as a Pockel cell and then injected into a ring cavity 112. The output of the cavity 112 may be detected by a detector 114 for display onto the oscilloscope 118. The single laser input frequency in this system is converted into a series of sidebands separated by a fundamental frequency that is a function of the modulator driver 110.

This system of cavity linewidth measurement requires two horizontal measurements, but does not require the use of free spectral range. The modulation frequency is at least five times the cavity linewidth to produce an output display with several widely separated side bands. The full width at half-maximum of one peak is measured as is the separation between two adjacent peaks. These are the only two horizontal measurements required to obtain cavity linewidth.

All the techniques disclosed herein draw on a split frequency source where adjacent modes are separated by a known quantity. The embodiments shown herein have achieved this through use of a periodically modulated signal, where the periodic modulation is aided by use of an electro-optical modulator. It is understood and known in the art that two-(or more)mode laser sources exist and such a two-mode laser source could be substituted in the configurations shown, allowing elimination of a periodic modulator. For example, a Zeeman laser causes frequency splitting between adjacent modes. As long as the frequency splitting from the source laser splits the modes produced by a known frequency, the techniques disclosed herein for measuring cavity linewidth will provide improved results.

Therefore, while certain embodiments have been disclosed herein, the applicants do not intend that the appended claims be limited to these specific embodiments, but rather expanded to include techniques which use a split frequency laser source.

What is claimed is:

1. A method of measuring cavity linewidth of a passive cavity, comprising the steps of:
   periodically modulating an output coherent radiation signal from a swept frequency laser, deriving a periodically modulated output coherent radiation signal;
   separating said periodically modulated output coherent radiation signal into a series of sideband coherent radiation signals;
   injecting said sideband signals into a passive cavity;
   detecting cavity output radiation signals from said passive cavity;
   processing said detected cavity output radiation signals for analysis on a display terminal;
   whereby, the cavity linewidth may be derived.

2. The method of measuring cavity linewidth of claim 1, additionally comprising the step of:
   viewing the cavity output radiation signals on said display terminal, said output signals on said display terminal including a plurality of peaks separated by a frequency which is a function of a modulation rate at which said output coherent radiation signals from said swept frequency laser are periodically modulated.

3. The method of measuring cavity linewidth of claim 2, wherein:
   adjacent peaks of said plurality of peaks are separated sufficiently to have minimal overlap.

4. A method of measuring cavity linewidth of a passive cavity, comprising the steps of:
   periodically modulating an output coherent radiation signal from a swept frequency laser source, deriving a modulated cavity input signal which is divided into a pair of balanced sidebands, a first sideband downshifted and a second sideband upshifted in frequency from a carrier frequency;
   eliminating said carrier frequency;
   injecting said pair of balanced sidebands into said passive cavity;
   detecting an output radiation signal from said passive cavity and presenting said output signal on a visual output display; and
   measuring cavity linewidth using only vertical image data present on the visual output display.

5. A method of measuring cavity linewidth of a passive resonator, comprising the steps of:
   injecting into said passive resonator a coherent split frequency radiation signal, said split frequency radiation signal being divided into a plurality of modes adjacent to one another and separated by a known uniform frequency splitting which is a function of resonator length;
   detecting an output radiation signal derived from the passive resonator being measured;
   processing said detected output radiation signal for analysis on a display terminal;
   whereby, the cavity linewidth of the passive resonator may be determined.

6. The method of measuring cavity linewidth of a passive resonator of claim 5, additionally comprising the steps of:
   showing a double peak unmodulated envelope on said display terminal;
   measuring the height of one of said peaks and the dip between said double peaks to establish a first ratio;
   converting said first ration to a second ratio; and
   multiplying said second ration by a frequency of said signal;
   whereby, cavity linewidth may be derived.

7. The method of measuring cavity linewidth of claim 5, additionally comprising the steps of:
   showing a double peak modulated envelope on said display terminal;
   comparing the height of a peak on the bottom of said envelope to the height of a dip between said double peaks on the top of said envelope and noting the frequency of said signal when the height and dip match; and
   dividing said frequency of said signal by a predetermined ratio when the height and dip match to obtain said cavity linewidth.

8. The method of measuring linewidth of claim 5, additionally comprising the steps of:
   showing a plurality of separated peaks on said display terminal;
   measuring the full width at half-maximum of one of said peaks and the distance between it and an adjacent peak; and
   establishing said cavity linewidth therefrom.

9. A method of measuring cavity linewidth of a passive cavity, comprising the steps of:
   periodically modulating an output coherent radiation signal from a swept frequency laser source, deriving a modulated cavity input signal which is divided into a pair of balanced sidebands, a first sideband downshifted and a second sideband upshifted in frequency from a carrier frequency;
   eliminating said carrier frequency;
   injecting said pair of balanced sidebands into said passive cavity; and
   detecting an output radiation signal from said passive cavity and presenting the output radiation signal on a visual output display.

* * * * *